US010583312B2

(12) United States Patent
Ono et al.

(10) Patent No.: US 10,583,312 B2
(45) Date of Patent: Mar. 10, 2020

(54) PARTICLE THERAPY SYSTEM

(71) Applicant: Hitachi, Ltd., Tokyo (JP)

(72) Inventors: Daisuke Ono, Tokyo (JP); Takayoshi Matsushita, Tokyo (JP); Isao Furuse, Tokyo (JP); Takao Kidani, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/878,464

(22) Filed: Jan. 24, 2018

(65) Prior Publication Data

US 2018/0264287 A1 Sep. 20, 2018

(30) Foreign Application Priority Data

Mar. 16, 2017 (JP) ................................ 2017-051558

(51) Int. Cl.
*A61N 5/10* (2006.01)
(52) U.S. Cl.
CPC ........... *A61N 5/1049* (2013.01); *A61N 5/103* (2013.01); *A61N 5/1069* (2013.01); *A61N 5/1081* (2013.01); *A61N 5/107* (2013.01); *A61N 5/1079* (2013.01); *A61N 2005/1058* (2013.01); *A61N 2005/1061* (2013.01); *A61N 2005/1074* (2013.01); *A61N 2005/1087* (2013.01)
(58) Field of Classification Search
CPC .... A61N 5/1049; A61N 5/103; A61N 5/1069; A61N 5/1081; A61N 5/107; A61N 5/1076; A61N 2005/1058; A61N 2005/1061; A61N 2005/1074; A61N 2005/1087
See application file for complete search history.

(56) References Cited

U.S. PATENT DOCUMENTS 5,446,548 A * 8/1995 Gerig ...................... A61B 6/08
250/462.1
2005/0029472 A1 2/2005 Ueno et al.
(Continued)

FOREIGN PATENT DOCUMENTS

JP 2005-027681 A 2/2005
JP 2011-072457 A 4/2011

OTHER PUBLICATIONS

Extended European Search Report received in corresponding European Application No. 18154604.5 dated Jun. 22, 2018.

*Primary Examiner* — Nicole M Ippolito
*Assistant Examiner* — Sean M Luck
(74) *Attorney, Agent, or Firm* — Mattingly & Malur, PC

(57) ABSTRACT

A treatment bed arranged in a tip direction of an irradiation nozzle and constructed movably, a treatment information system that manages prescription data, a treatment control system that receives a target position stored in the treatment information system to cause a main display system to display the target position, a pendant to input a movement command for the treatment bed, the main display system that receives the target position of the treatment bed from the treatment control system and displays an actual position of the treatment bed, and a patient positioning support system that calculates correction values for the target position thereof to provide the correction values to the treatment control system and the pendant are included, wherein the treatment control system sends the target position thereof to the treatment information system at a period shorter than an operation sequence thereof and stores initial values to be sent in advance.

4 Claims, 4 Drawing Sheets

(56) References Cited

U.S. PATENT DOCUMENTS

| | | | |
|---|---|---|---|
| 2005/0139787 A1 | 6/2005 | Chiba et al. | |
| 2005/0283068 A1* | 12/2005 | Zuccolotto | A61B 5/0555 600/410 |
| 2006/0063999 A1* | 3/2006 | Herron | A61N 5/1049 600/407 |
| 2008/0232664 A1 | 9/2008 | Nagamine et al. | |
| 2011/0135190 A1* | 6/2011 | Maad | A61B 6/0407 382/154 |
| 2011/0172526 A1* | 7/2011 | Lachaine | A61B 8/085 600/439 |
| 2012/0071758 A1* | 3/2012 | Lachaine | A61B 8/085 600/439 |
| 2013/0178690 A1* | 7/2013 | Masumoto | A61N 5/1037 600/1 |
| 2013/0343511 A1* | 12/2013 | Shukla | A61B 6/032 378/6 |
| 2014/0205167 A1* | 7/2014 | Kleiner | A61B 6/032 382/131 |
| 2015/0126796 A1* | 5/2015 | Yan | A61B 6/03 600/1 |
| 2016/0175617 A1* | 6/2016 | Spatola | A61N 5/1071 600/1 |
| 2016/0287907 A1 | 10/2016 | Michaud et al. | |

\* cited by examiner

PARTICLE THERAPY SYSTEM

BACKGROUND OF THE INVENTION

1. Field of the Invention

The present invention relates to a particle therapy system.

2. Description of the Related Art

As the background art of the present invention, for example, the technology disclosed in JP 2011-72457 A is known. This gazette discloses that, to improve positioning precision using soft tissue information of organs or the like when a radiation therapeutic bed is positioned, a bed on which a subject is placed, a bed positioning apparatus that positions the bed for radiation therapy, an X-ray generator that generates X rays, and an X-ray imaging apparatus including an X-ray receiver that receives X rays from the X-ray generator are included, and the bed positioning apparatus generates bed positioning data based on first X-ray image data imaged by the X-ray imaging apparatus and soft tissue projection image data generated from X-ray computed tomography image data acquired during treatment planning.

Also, for example, JP 2005-27681 A discloses, as an example of an irradiation room in a radiation therapy system, an irradiation room constructed of a hard switch to demand a beam to an accelerator control room, a gantry that irradiates a target volume of a patient from any direction, a therapeutic bed to fix the patient, a maze-like passage to block radiation, and a protection door.

SUMMARY OF THE INVENTION

For the operation of a radiation therapy system, as shown in JP 2011-72457 A, high-precision positioning work of a patient is done before treatment is started. In this case, a worker is desirably near a patient to be able to directly assist the patient. On the other hand, as shown in JP 2005-27681 A, the worker needs to monitor or control treatment equipment and the like in a operation room during irradiation of radiation.

It is also known in many cases that in the operation time by a radiation therapy system, the time needed for positioning is longer than the time thereafter for irradiation of radiation. In such a radiation therapy system, to improve efficiency of treatment, it is desirable to be able to limit particularly lengthening of preparation periods of treatment in both of the operation room and the treatment room by presenting information without delay following an operational procedure of the worker.

The present invention provides a particle therapy system capable of presenting information without delay following an operational procedure of the worker in both of the operation room and the treatment room and particularly limiting lengthening of preparation periods of treatment.

The present invention includes a plurality of means to solve the above problem and an example thereof is a particle therapy system including: an accelerator that generates a charged particle beam; an irradiation nozzle used for irradiation of the charged particle beam; a treatment bed arranged in a tip direction of the irradiation nozzle and constructed movably; a treatment information system that manages prescription data; a treatment control system that receives a target position stored in the treatment information system to cause a display system to present the target position; an irradiation control system that receives control parameters of the irradiation nozzle from the treatment control system to perform the control parameters; a pendant to input a movement command for the treatment bed; a patient positioning apparatus that controls the treatment bed based on the movement command; the display system that receives the target position of the treatment bed from the treatment control system and displays an actual position of the treatment bed; and a patient positioning support system that calculates correction values for the target position of the treatment bed to provide the correction values to the treatment control system and the pendant, wherein the treatment control system sends the target position of the treatment bed to the treatment information system at a period shorter than an operation sequence of the treatment control system and stores initial values to be sent in advance.

According to the present invention, information can be presented without delay following an operational procedure of the worker in both of the operation room and the treatment room and particularly lengthening of preparation periods of treatment can be limited.

DESCRIPTION OF THE PREFERRED EMBODIMENTS

Hereinafter, an embodiment of the present invention will be described using FIGS. 1 to 4. Incidentally, an application example of a particle therapy system 100 will be described below, but the present invention is not limited to such an example and can similarly be applied to various kinds of radiation therapy systems including X rays, gamma rays, and electron beams.

Figure 1:
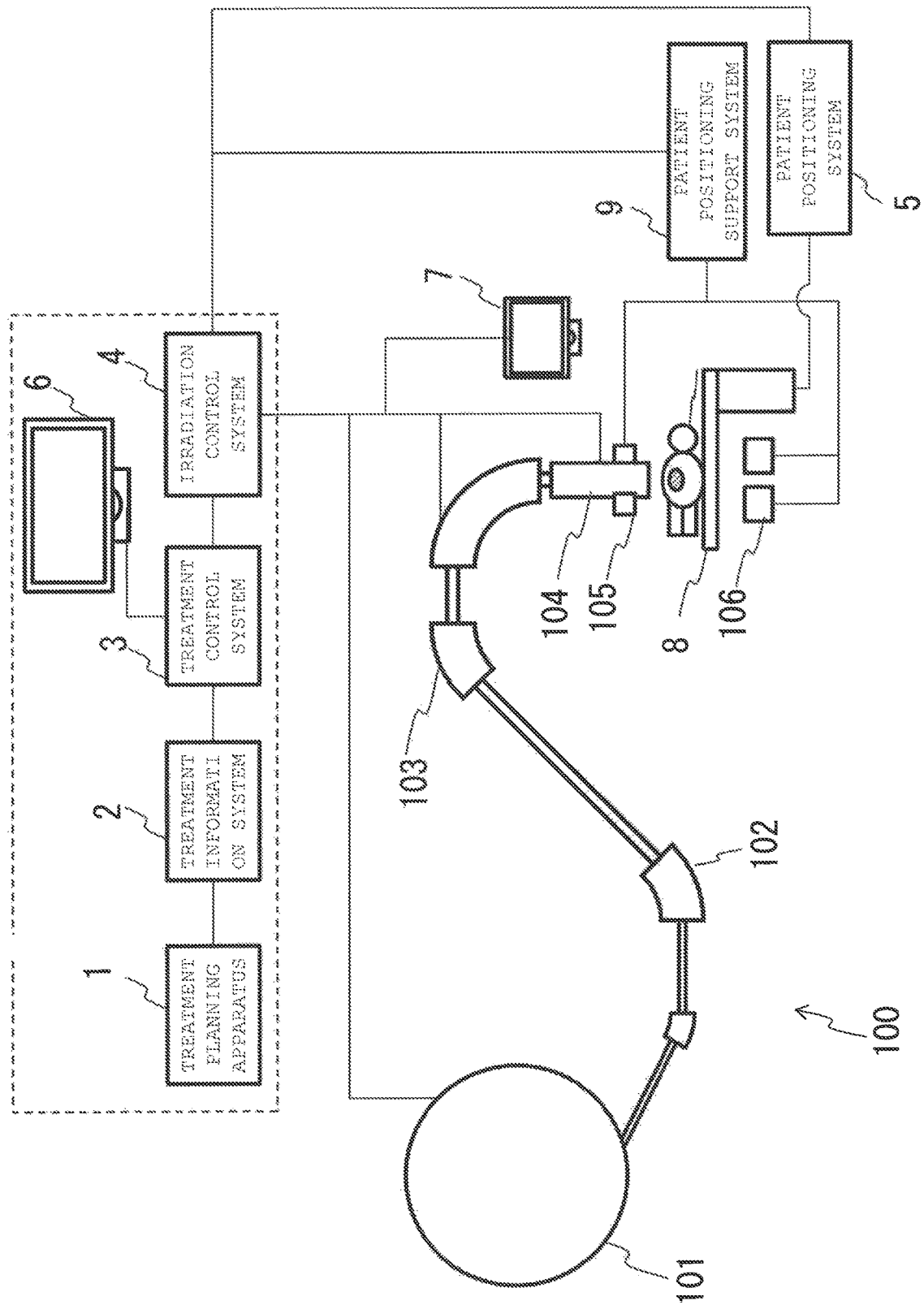
FIG. 1 shows an overall image of a particle therapy system as an embodiment of the present invention.
Figure 2:
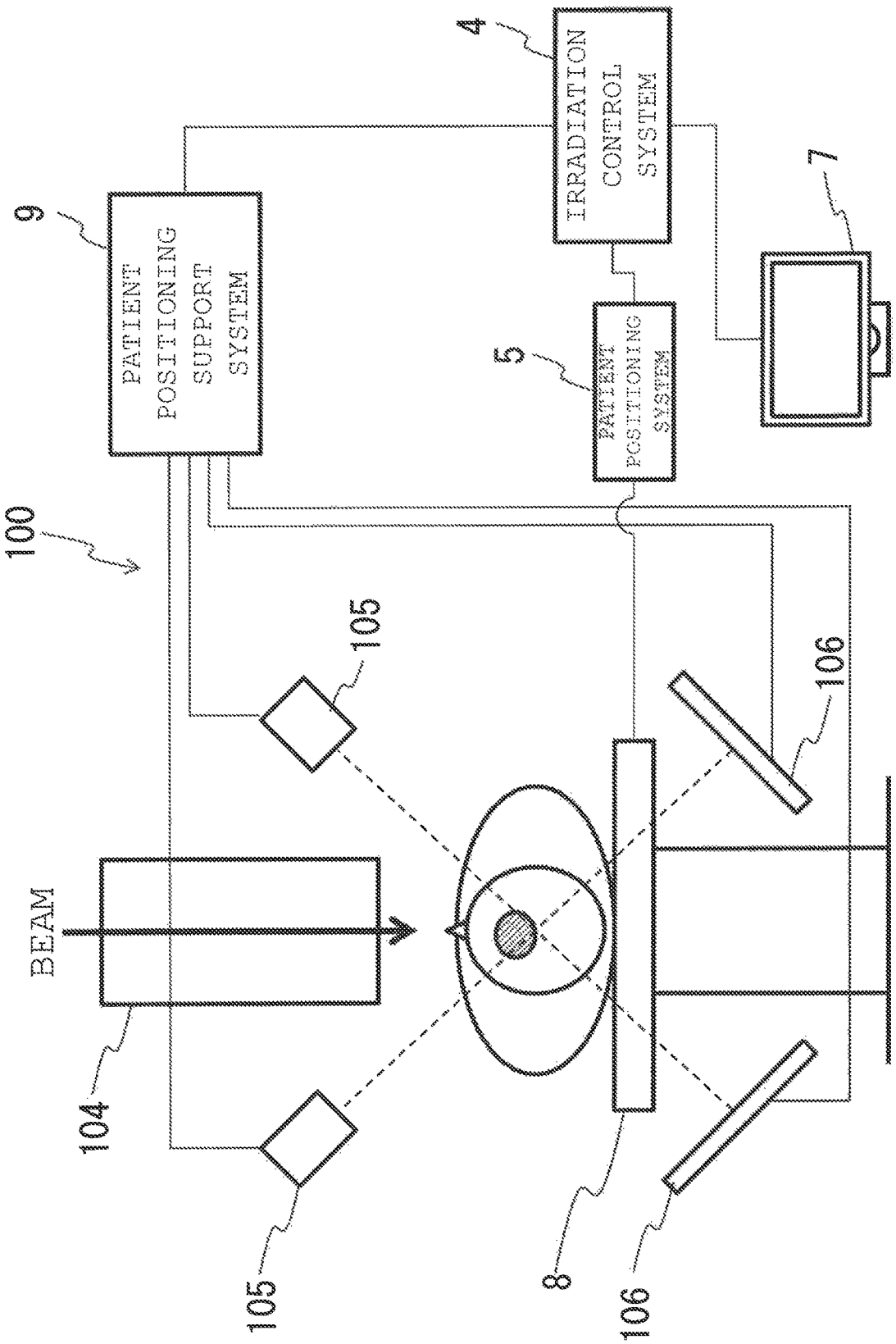
FIG. 2 shows devices and systems related to patient positioning in the particle therapy system.

First, the basic structure of the particle therapy system 100 will be described using FIGS. 1 and 2. FIG. 1 shows an overall image of the particle therapy system 100. FIG. 2 shows devices and systems related to patient positioning in the particle therapy system 100.

<Overall Image of the Particle Therapy System 100>

As shown in FIG. 1, the particle therapy system 100 takes a charged particle beam (hereinafter, simply called a beam) accelerated up to predetermined kinetic energy by an accelerator 101 such as a synchrotron into a high energy beam transport 102 to irradiate a target volume as an irradiation target fixed to a treatment bed 8 therewith via a (rotating) gantry 103 and an irradiation nozzle 104 mounted on the (rotating) gantry 103. The (rotating) gantry 103 rotates surroundings of the patient around a rotation axis to enable beam irradiation to the patient from a plurality of different directions. Incidentally, the system may be such that a beam is irradiated from a fixed direction by omitting the configuration of the (rotating) gantry 103.

When a beam is irradiated, as shown in FIGS. 1 and 2, the patent is arranged on the treatment bed 8. An X-ray imaging apparatus including an X-ray generator 105 and an X-ray detector 106 is arranged around the treatment bed 8 as a portion of the patient positioning apparatus. Instead of the X-ray imaging apparatus, a means capable of measuring the position of tumor such as a cone beam CT apparatus, a proton beam CT apparatus, an ultrasonic imaging apparatus, and a magnetic resonance imaging apparatus may be adopted as a portion of the patient positioning apparatus.

The operation of each device described above is controlled by various control apparatuses and control systems (hereinafter, called control system) shown in FIG. 1. These control systems are constructed like stretching over the treatment room and the operation room and control devices arranged in each room are mutually communicably constructed and used to issue operation commands to the accelerator 101, magnets, the (rotating) gantry 103, the treatment bed 8 and the like.

Incidentally, the treatment room refers to space used to irradiate the patient with radiation and is typically space surrounded by shielding walls using concrete or the like and in the space, at least the treatment bed 8 and an irradiation port and an irradiation nozzle tip portion to provide radiation are provided. The operation room is not limited to a case of being able to spatially shield completely from the treatment room and is space in which a computer to control each device and a monitor to monitor the state of each device are provided in a concentrated manner and the operation room is provided in a position that does not hinder treatment.

Figure 3:
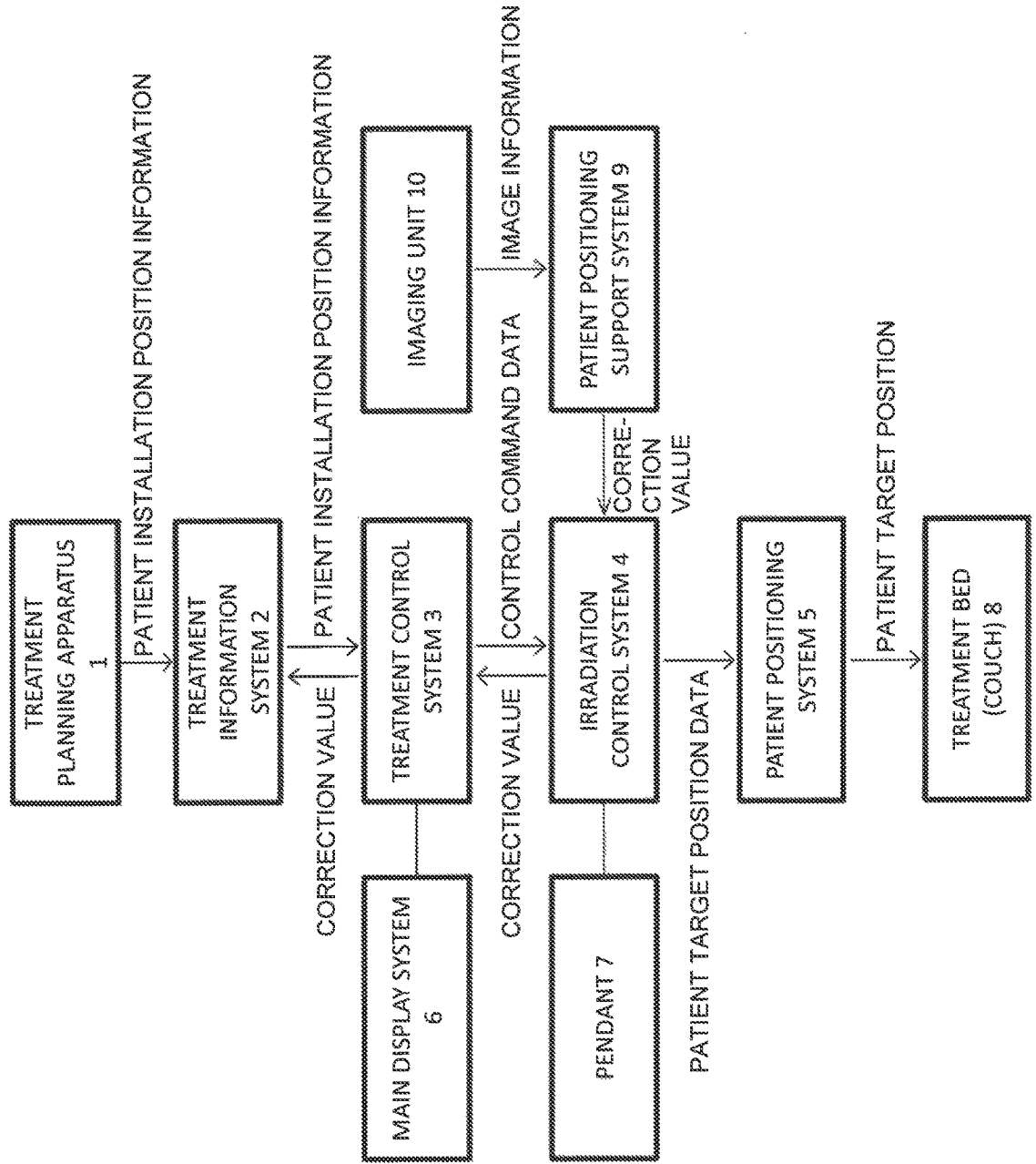
FIG. 3 shows an outline configuration of control systems related to the particle therapy system according to an embodiment.

In the operation room, many control devices to control the particle therapy system 100 are arranged. However, some devices including a pendant 7 described below are arranged in the treatment room because of work to be performed on the patient's side. For the treatment, the worker performs work needed in each of the treatment room and the operation room and the control system has a means to present information to the worker in both of the treatment room and the operation room to make such work executable. Hereinafter, as an example of such a control system, a system related to positioning of the patient will be described using FIGS. 1 and 3. FIG. 3 shows an outline configuration of control systems related to the particle therapy system 100 according to the present embodiment.

<Control System Related to Positioning of the Patient>

As shown in FIG. 1, in the particle therapy system 100 shown in the present embodiment, the control system related to positioning of the patient is a system in which a treatment planning apparatus 1, a treatment information system 2, a treatment control system 3, an irradiation control system 4, and a patient positioning system 5 are mutually communicably constructed in this order from the top level. As shown in FIGS. 1 and 3, a main display system 6 is connected to the treatment control system 3, the pendant 7 and a sub-display system (not shown) arranged inside the treatment room are connected to the irradiation control system 4, and the treatment bed 8 is connected to the patient positioning system 5.

Incidentally, the pendant 7 is an interface for operation of the particle therapy system 100 provided in the treatment room and an operator performs work in the treatment room using the pendant 7. The pendant 7 has a display unit that is different from the main display system 6 as a portion thereof and is configured to be able to check work and operation conditions in the treatment room in real time.

The irradiation control system 4 is connected to a patient positioning support system 9 to acquire the target position (correction value) in which installation errors of the patient are corrected from the patient positioning support system 9 (PIAS). Incidentally, the patient positioning support system 9 has a function to calculate a correction value of the treatment bed 8 based on an image acquired by an imaging unit 10 such as the X-ray imaging apparatus including the X-ray generator 105 and the X-ray detector 106 provided in the treatment room and to update the target position.

Each system may be implemented on one computer or configured via a network to perform calculations and the like on a server.

The main function of each system is as follows: The treatment planning apparatus 1 has a function to perform a simulation to determine the position and range inside the body to be irradiated with radiation and a dose distribution of radiation to be irradiated with. The particle therapy system 100 operates following an operation result (treatment planning) of the treatment planning apparatus 1.

The treatment information system 2 is a system in which patient information such as the patient's name and age is registered and has an input/output function of the selection of the patient to be treated, schedule management of treatment, and progress information treatment and when treatment is started, the target patient is first selected from the present system.

The treatment control system 3 and the irradiation control system 4 have a function to output commands to each device constituting the particle therapy system 100 and an interlock function. The irradiation control system 4 mainly controls devices constituting the particle therapy system 100. The treatment control system 3 has a wider range of control targets including the irradiation control system 4 and gate opening/closing of the treatment room. The irradiation control system 4 is connected to an input/output interface called the pendant 7 arranged in the treatment room.

The main display system 6 is what is called a human machine interface. The main display system 6 has a function to receive and display information to be presented to physicians, medical physicists, and nurses from the treatment control system 3 and also a function to display the actual position of the treatment bed 8. The main display system 6 also includes an input/output unit to issue commands to the treatment control system 3. The main display system 6 may also be provided as an interface of the treatment information system 2 or the treatment control system 3.

The pendant 7 is an input/output interface provided in the treatment room and, for example, the worker can issue a movement command of the treatment bed 8 to the patient positioning system 5 via the pendant 7.

The patient positioning system 5 has a function to mainly perform position management and movement control of the treatment bed 8. Typically, the patient positioning system 5 has a function to move the treatment bed 8 on which the patient is actually arranged toward the position (the planned position or target position) stored in the treatment planning apparatus 1. The treatment bed 8 is moved by operation parameters to be performed by a support system (for example, a robot arm) of the treatment bed 8 being calculated based on a deviation of the actual position from the target position and these operation parameters being performed.

Actually, however, bending due to patient's weight or a positional change of organs between when the treatment was planned and when the patient is treated may occur and thus, even if movement parameters of the treatment bed 8 are performed just as treatment was planned, a slight difference arises between the target position and the actual position. Such an error is reduced to the extent that no problem is caused for treatment by the patient positioning support system 9.

The patient positioning support system 9 has a function to determine a difference between the actual position and the target position when treatment was planned by measuring the actual position of the target immediately before irradiation using the imaging unit 10 such as an X-ray imaging apparatus including the X-ray generator 105 and the X-ray detector 106 and to update the target position. In this case, information of the target position is in accordance with the degree of freedom of the treatment bed 8 and is given, for example, as parameters (x, y, z, Pitch, Roll, and Yaw) of six axes including space coordinates related to three orthogonal axes and a rotation angle of each axis.

If the system is a typical one like the particle therapy system 100 shown in FIG. 1, the treatment planning apparatus 1 to the patient positioning system 5 and the patient positioning support system 9 are desirably arranged in the operation room. If all or a portion of these systems is provided in a position apart from the operation room, the particle therapy system 100 can be operated while viewing the situation of the treatment room by the main display system 6 connected to that control system and an input unit being provided in the operation room. Therefore, the control system may be configured as described above.

Figure 4:
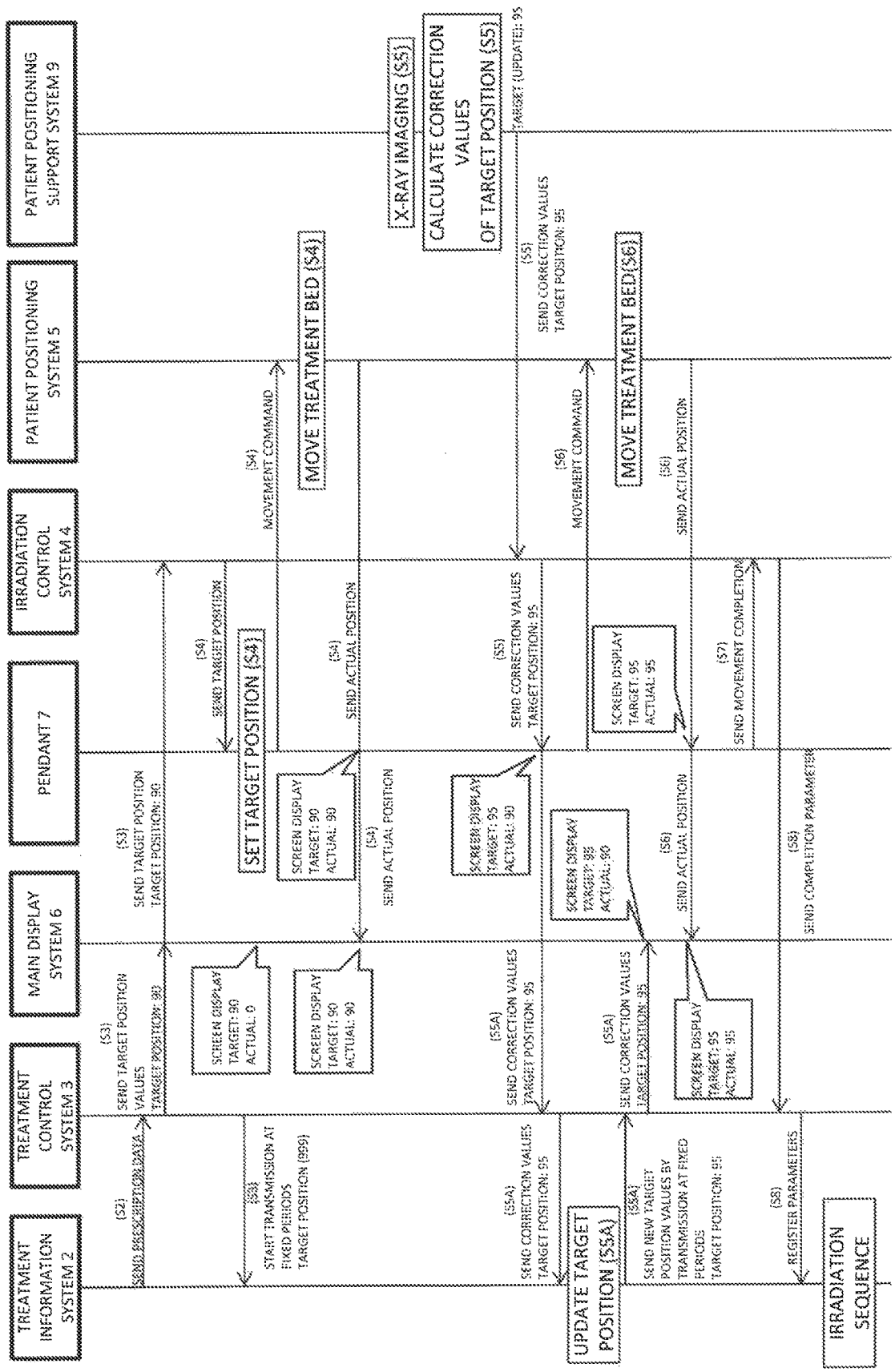
FIG. 4 shows an overview of a positioning sequence of the control systems according to an embodiment.

The flow of positioning using the above control systems will be described using FIG. 4. FIG. 4 shows an overview of a positioning sequence of the control systems according to the present embodiment.

<Positioning Flow>

The worker has prescription data including installation position information of the patient sent from the treatment planning apparatus 1 to the treatment information system 2 via the interface of the treatment information system 2 (Step 1). The prescription data includes information needed for treatment such as the dose distribution of radiation with which the patient should be irradiated, the target position where the patient is to be installed, and control command data of each device.

Next, the patient to be treated is selected from Work List Manager (WLM) of the treatment information system 2 and, as shown in FIG. 4, prescription data of the corresponding patient is sent to the treatment control system 3 (Step 2).

Then, the treatment control system 3 sends the target position values of the treatment bed 8 included in the prescription data received from the treatment information system 2 to the main display system 6 (step 3). At this point, the treatment bed 8 does not move and so is the actual position of the treatment bed 8 is the initial values (for example, all zero) and the main display system 6 displays the target position stored in the treatment information system 2 and the actual position in an initial value state. In parallel, the treatment control system 3 sends control command data of each device and the target position of the treatment bed 8 from the prescription data to the irradiation control system 4. Further, the transmission of the target position of the treatment bed 8 from the treatment control system 3 to the treatment information system 2 is started at fixed periods. The transmission at fixed periods is performed at a period shorter than an operation sequence of the treatment control system 3. Also, the above initial values are transmitted to the treatment information system 2 at fixed periods until correction values of the treatment bed 8 are received in Step 5A described below. The transmission at fixed periods is performed at least until the setup operation of the patient is completed.

Incidentally, the target position values and the target position transmitted at the stage of Step 3 are any initial values provided to the treatment control system 3 in advance. The initial values are values that cannot be adopted as the target position and, for example, values exceeding movable limit values of the treatment bed 8. The treatment information system 2 stores the range of values that can be adopted as the target position in advance and controls systems including the treatment control system 3 as a low-order system and lower so that such initial values are not set as a new target position.

When, in Step 3, the target position is received from the treatment control system 3, the irradiation control system 4 sends the target position to the pendant 7. The worker issues a movement command to the treatment bed 8 so that the actual position matches the target position displayed on the pendant 7 (Step 4). Also, information of the actual position is reflected in the main display system 6.

When the treatment bed 8 reaches the target position, the patient is photographed by the imaging unit 10. Based on the photographed image information, a difference from the target position when treatment was planned is calculated and correction values for the target position are calculated. The correction values are sent to the irradiation control system 4 and the target position of the treatment bed 8 is updated. The updated target position is also displayed on the pendant 7 (Step 5).

After checking the updated target position, the worker operates the pendant 7 to issue a movement command to the treatment bed 8 so that the actual position matches the new target position. The command input via the pendant 7 is provided to the treatment bed 8 via the irradiation control system 4 and the treatment bed 8 starts to move following the movement command. While the treatment bed 8 moves, data of the actual position of the treatment bed 8 and the updated target position is displayed on the interface of the pendant 7 from the irradiation control system 4 (Step 6).

After the treatment bed 8 reaches the target position, the irradiation control system 4 sends the target position updated in parallel to the treatment control system 3 (Step 5A). The treatment control system 3 having received the information sends the updated target position to the treatment information system 2 as a high-order system using periodic transmission started in Step 3. The treatment information system 2 records the updated target position and also issues a command of new target position values to the treatment control system 3 so that the new target position is reflected in the main display system 6. As a result, the updated target position can be presented by both of the main display system 6 and the pendant 7 so that deviations of update timing of display content can be limited. After Step 5A, instead of initial values, correction values sent from the irradiation control system 4 are transmitted to the treatment information system 2 at fixed periods.

When the movement of the treatment bed 8 is completed, the worker inputs a positioning completion command via the pendant 7. The positioning completion command is output from the pendant 7 to the irradiation control system 4 and the irradiation control system 4 stores information of the target position and the actual position of the treatment bed 8 when positioning is completed (parameters when positioning is completed) (Step 7).

When the positioning sequence is completed, the updated target position is sent from the treatment information system 2 to the main display system 6 via the treatment control system 3 and displayed there to complete the setup operation of the patient (Step 8).

<Effect>

As described above, the treatment information system 2 stores the range of values that can be adopted as the target position in advance and thus, safety is ensured by controlling low-order systems so that initial values handed over from the treatment control system 3 are not set as a new target position. The presentation of unnecessary information to the worker can be avoided and deterioration of work efficiency of the worker can be reduced by the control being exercised by the treatment information system 2 so that initial values are not reflected in the main display system 6.

The updated target position can be presented by both of the main display system 6 and the pendant 7 so that deviations of update timing of display content can be limited. As a result, unnecessary checking caused by differences of information presented to the worker and a waiting time can be reduced so that a contribution can be made to improving work efficiency. That is, because appropriate information can be presented to the worker without delay following an operational procedure in both of the operation room and the treatment room, unnecessary checking and a waiting time are reduced and particularly lengthening of preparation periods of treatment can be limited.

<Others>

The present invention is not limited to the above embodiment and it is possible to make various modifications and find new applications thereof. The above embodiment has been described in detail to describe the present invention so as to be understood more easily and not all the components described above are necessarily included.

What is claimed is:

1. A particle therapy system comprising:
an accelerator that generates a charged particle beam;
an irradiation nozzle that irradiates the charged particle beam;
a treatment bed that is moveable and has a patient arranged thereon;
a treatment information system that manages prescription data including target position information of the treatment bed;
a treatment control system, connected to the treatment information system, that receives the target position information from the treatment information system and displays the target position information on a display system;
an irradiation control system, connected to the treatment control system, that receives control parameters of the irradiation nozzle from the treatment control system to control the irradiation nozzle;
a pendant, including a display, configured to receive a movement command for moving the treatment bed;
a patient positioning system, connected to the irradiation control system, that controls movement of the treatment bed based on the movement command;
an X-ray imaging unit; and
a patient positioning support system that controls the X-ray imaging unit to acquire an image of the patient arranged on the bed,
wherein the irradiation control system receives the target position information and sends the target position control information to the pendant,
wherein the pendant receives the movement command for moving the treatment bed while concurrently displaying actual position information of the treatment bed as the treatment bed is moved based on the movement command and the target position information of the treatment bed,
wherein the patient positioning support system calculates correction values for correcting the target position information of the treatment bed based on the image acquired by the X-ray imaging unit, calculates updated target position information and provides the updated target position information to the treatment control system and the pendant,
wherein the display of the pendant concurrently displays the updated target position information and the actual position information of the treatment bed, and
wherein the treatment control system periodically sends, at predetermined fixed periods of time, the target position information including the updated target position information of the treatment bed to the treatment information system.

2. The particle therapy system according to claim 1, wherein the pendant is disposed in a treatment room and the display system is disposed in an operation room that is next to the treatment room.

3. The particle therapy system according to claim 2, wherein the treatment control system periodically transmits initial values registered in advance to the treatment information system until correction values sent from the patient positioning system, which are received after the target position information contained in the prescription data is displayed on the display system, and wherein after the correction values are received, instead of the initial values, the correction values are transmitted to the treatment information system.

4. The particle therapy system according to claim 3, wherein the treatment information system sends new target position information to the treatment control system and he display system displays the new target position information when the updated target position transmitted from the treatment control system is within an operation range of the treatment bed, and wherein the treatment information system does not send the new target position information to the treatment control system when the updated target position transmitted from the treatment control system is not within the operation range of the treatment bed.

* * * * *